US011857306B1

(12) United States Patent
Posse

(10) Patent No.: US 11,857,306 B1
(45) Date of Patent: Jan. 2, 2024

(54) CONCURRENT MRSI AND FMRI

(71) Applicant: UNM Rainforest Innovations, Albuquerque, NM (US)

(72) Inventor: Stefan Posse, Albuquerque, NM (US)

(73) Assignee: UNM Rainforest Innovations, Albuquerque, NM (US)

(*) Notice: Subject to any disclaimer, the term of this patent is extended or adjusted under 35 U.S.C. 154(b) by 121 days.

(21) Appl. No.: 17/240,671

(22) Filed: Apr. 26, 2021

Related U.S. Application Data

(63) Continuation of application No. 16/442,301, filed on Jun. 14, 2019, now abandoned.

(60) Provisional application No. 62/685,725, filed on Jun. 15, 2018.

(51) Int. Cl.
| | |
|---|---|
| *G01V 3/00* | (2006.01) |
| *A61B 5/055* | (2006.01) |
| *A61B 5/00* | (2006.01) |
| *G01R 33/48* | (2006.01) |
| *G01R 33/50* | (2006.01) |

(52) U.S. Cl.
CPC ............ *A61B 5/055* (2013.01); *A61B 5/0042* (2013.01); *G01R 33/4806* (2013.01); *G01R 33/50* (2013.01); *G01R 33/4828* (2013.01); *G06T 2207/10088* (2013.01)

(58) Field of Classification Search
CPC .............. G01R 33/3415; G01R 33/543; G01R 33/5659; G01R 33/36; A61B 5/055
USPC ........................................................ 324/309
See application file for complete search history.

(56) References Cited

U.S. PATENT DOCUMENTS

| | | | |
|---|---|---|---|
| 5,363,036 A | 11/1994 | Mansfield | |
| 5,786,692 A * | 7/1998 | Maier | G01R 33/56341 324/309 |
| 6,320,381 B1 | 11/2001 | Hennig | |
| 10,406,384 B2 * | 9/2019 | Köhler | A61B 5/748 |
| 2009/0285463 A1 | 11/2009 | Otazo et al. | |
| 2010/0026294 A1 * | 2/2010 | Lustig | G01R 33/5616 324/307 |
| 2011/0221439 A1 | 9/2011 | Posse | |
| 2012/0286777 A1 | 11/2012 | Frost et al. | |
| 2012/0313641 A1 * | 12/2012 | Labadie | G01R 33/485 324/309 |
| 2013/0253305 A1 * | 9/2013 | Koktzoglou | G01R 33/5607 600/410 |
| 2014/0107728 A1 | 4/2014 | Fried et al. | |
| 2014/0148657 A1 | 5/2014 | Hendler et al. | |

(Continued)

FOREIGN PATENT DOCUMENTS

JP 5268209 B2 * 8/2013

OTHER PUBLICATIONS

A. E. Amin; et al, "Integration of Water Referencing with Water Suppression for Absolute Quantification of High-Speed MR Spectroscopic Imaging.," in Proc. International Society for Magnetic Resonance in Medicine {ISMRM); 3 pages; Honolulu, HI, 2017, p. 5503.

(Continued)

*Primary Examiner* — Walter L Lindsay, Jr.
(74) *Attorney, Agent, or Firm* — MH2 TECHNOLOGY LAW GROUP LLP

(57) ABSTRACT

A method of obtaining multiple MRI contrasts of a subject comprising the steps of concurrently acquiring an MRSI and fMRI data in the same scan.

20 Claims, 11 Drawing Sheets

(56) References Cited

U.S. PATENT DOCUMENTS

| | | | |
|---|---|---|---|
| 2015/0042949 A1* | 2/2015 | Jeglorz | G01B 11/02 |
| | | | 356/497 |
| 2015/0253411 A1 | 9/2015 | Umeda | |
| 2016/0033605 A1 | 2/2016 | Stemmer et al. | |
| 2016/0120437 A1 | 5/2016 | Graham et al. | |
| 2017/0061588 A1 | 3/2017 | Lee et al. | |
| 2017/0238879 A1* | 8/2017 | Ducreux | A61B 5/369 |
| 2017/0261584 A1 | 9/2017 | James et al. | |

OTHER PUBLICATIONS

S. Posse, et al; "Proton echo-planar spectroscopic imaging of J-coupled resonances in human brain at 3 and 4 Tesla," Magn Reson Med, val. 58, pp. 236-244, 9 pages; Aug. 2007.

S. Posse, et al; "Enhancement of temporal resolution and BOLD sensitivity in real-time fMRI using multi-slab echo- volumar imaging," Neuroimage, val. 61, pp. 115-130, 16 pages; May 15, 2012, Elsevier.

S. Posse, et al; "A new approach to measure single-event related brain activity using real-time fMRI: Feasibility of sensory, motor, and higher cognitive tasks," Human Brain Mapping, val. 12, pp. 25-41, 17 pages; Jan. 2001; Wiley-Liss, Inc.

* cited by examiner

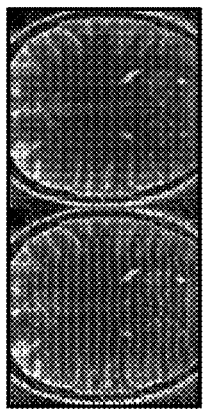
FIG. 6A
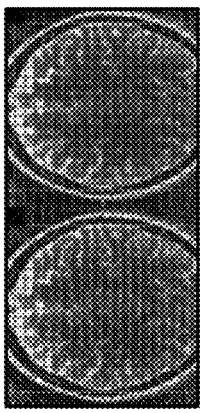
FIG. 6D
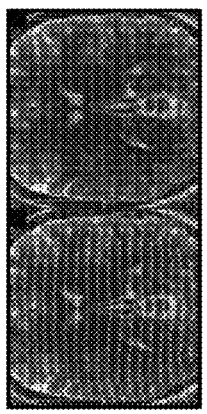
FIG. 6B
FIG. 6E
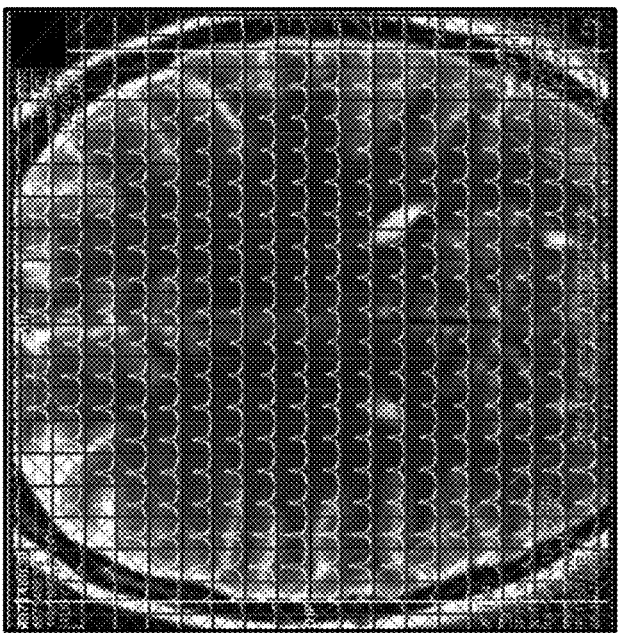
FIG. 6C
FIG. 6F
FIG. 6G
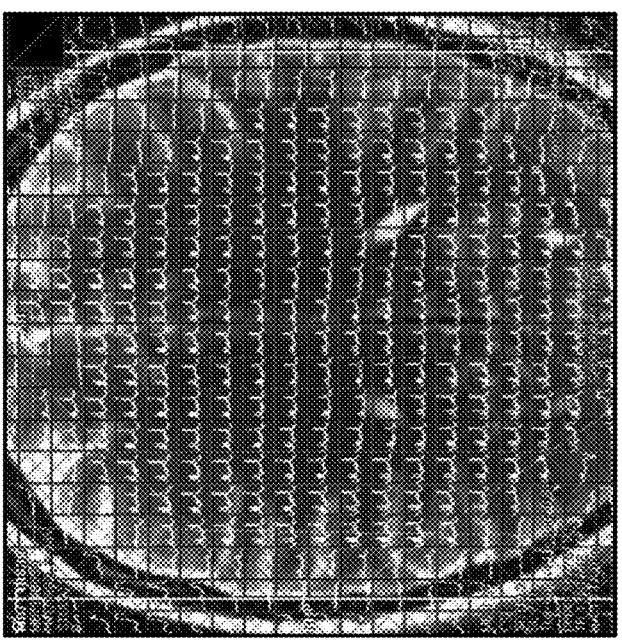
FIG. 6H

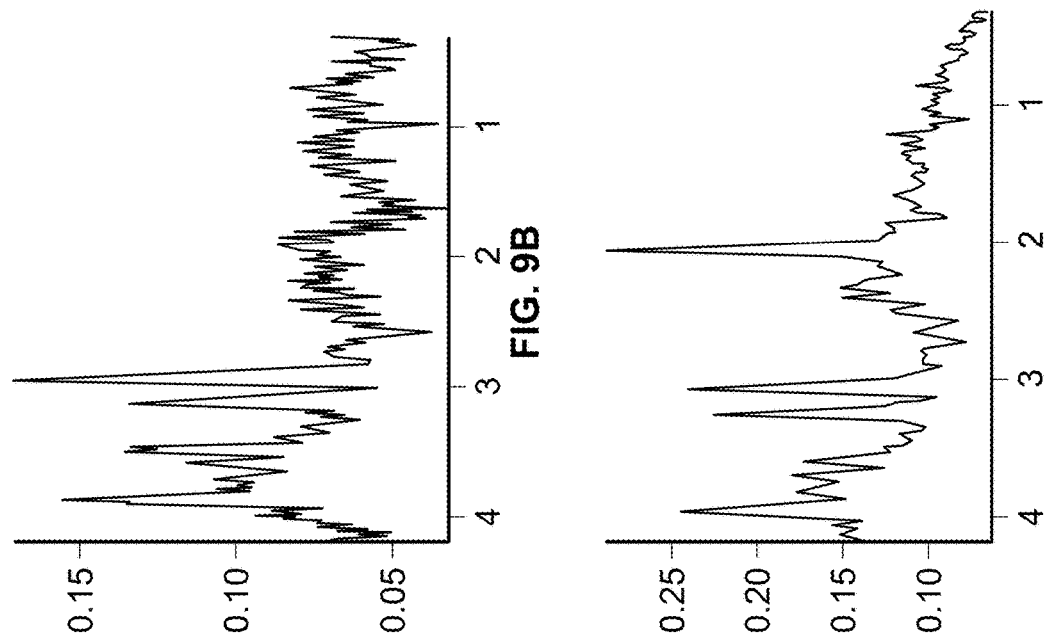
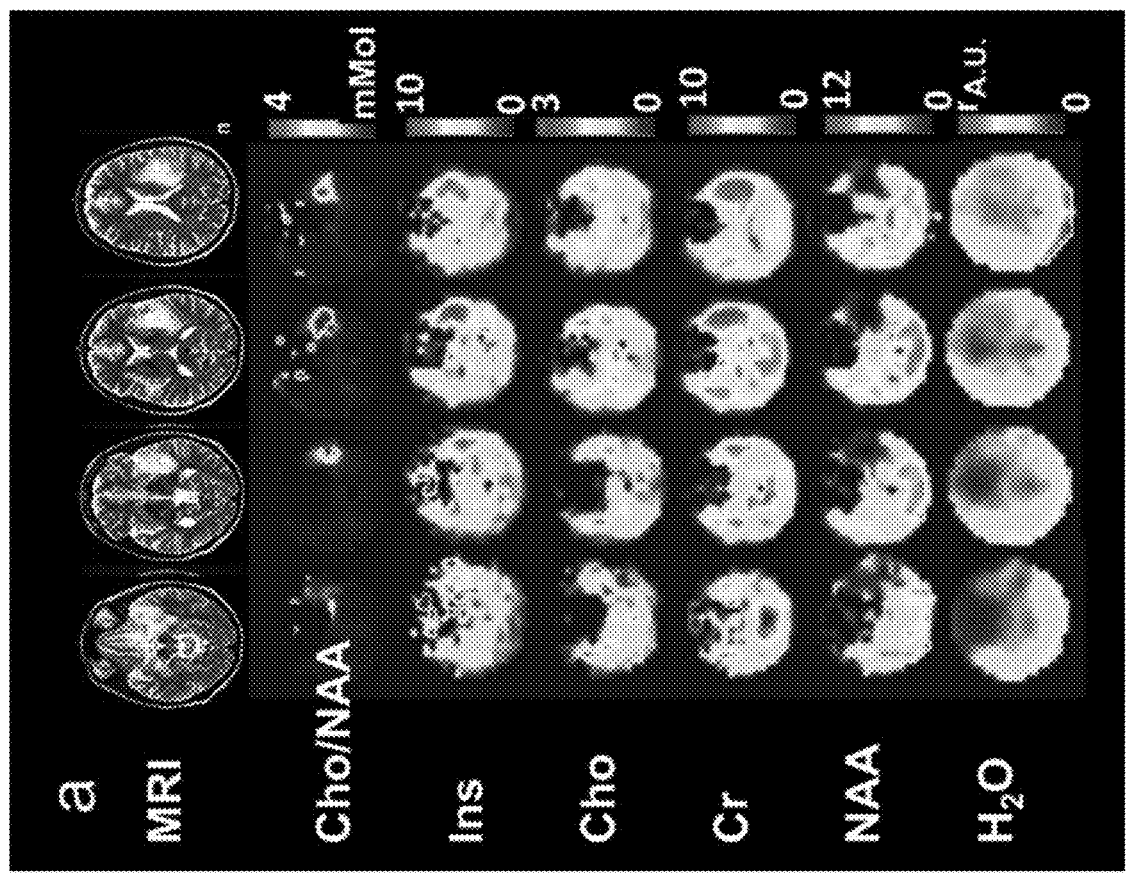
FIG. 9A
FIG. 9B
FIG. 9C

CONCURRENT MRSI AND FMRI

RELATED APPLICATIONS

This application is a continuation of U.S. Ser. No. 16/442,301 filed on Jun. 14, 2019, which claims priority to U.S. Provisional Ser. No. 62/685,725 filed on Jun. 15, 2018, which are both incorporated herein in their entirety.

STATEMENT REGARDING FEDERALLY SPONSORED RESEARCH & DEVELOPMENT

This invention was made with government support by the National Institutes of Health (NIH), grant 1R21EB011606-01A1. The government has certain rights in the invention.

INCORPORATION BY REFERENCE OF MATERIAL SUBMITTED ON A COMPACT DISC

Not applicable.

BACKGROUND OF THE INVENTION

Proton MR spectroscopic imaging (MRSI) in the clinical setting is time consuming with scan times ranging from several minutes to half an hour depending on spatial resolution and volume coverage. Functional MRI (fMRI) requires similar scan times depending on the tasks and spatial resolution. The long scan times of these modalities often preclude collecting MRSI and fMRI data in a single scanning session.

In addition, water suppression is an integral part of proton MR spectroscopic imaging (MRSI) and routinely used to suppress the overwhelming tissue water resonance to minimize the broad baseline of the water signal and associated gradient sideband artifacts. Multi-pulse $T_1$- and $B_1$ compensated water suppression schemes, such as water suppression enhanced through $T_1$ effects (WET) and water suppression with variable power radiofrequency (RF) pulses and optimized relaxation delays (VAPOR), are widely used to mitigate the effects of multiple water components with different $T_1$ values and degradation of water suppression due to $B_1$ inhomogeneity.

Water reference (WR) scans are routinely acquired in conjunction with MRSI to provide a concentration reference for quantifying metabolite signals. In addition, the strong water signal allows sensitive measurement of eddy current related phase changes that can be deconvolved from the metabolite signals to improve spectral quality. WR signals are typically acquired in a separate scan, which is time consuming. In conventionally phase-encoded MRSI, a WR acquisition may take as much time as the water-suppressed (WS) scan and, although the WR scan repetition time (TR) can be reduced to save time, the resulting $T_1$-saturation effects must be corrected. High-speed MRSI, using echo-planar or spiral gradient encoding, parallel imaging or hybrid encoding approaches, allows the WR scan to be acquired considerably faster. However, for volumetric metabolite mapping, the WR scan acquisition time is still on the order of the WS scan. Alternatively, the WR scan can be interleaved into the WS acquisition, although this elongates the minimum TR and requires acquisition of the WR scan using a partial flip angle.

In addition to interleaving a WR scan, it is possible to interleave a fMRI scan to concurrently assess metabolic changes during functional activation or to reduce overall scan time for multi-modal imaging. For example, a recent study demonstrated that insertion of a 3D echo-planar imaging (EPI) module into a semi-Laser MRS pulse sequence allowed concurrent acquisition of functional MRI (fMRI) and localized, single-voxel MRS during visual stimulation. Extending this approach to acquire combined fMRI and quantitative MRSI would be desirable both clinically and for research to assess the regional specificity of fMRI correlated metabolic differences as they provide complementary functional and metabolic information, for example to map eloquent cortex in the vicinity of brain lesions. However, the long scan times and considerable differences in spatial resolution of conventional fMRI and MRSI methods have been barriers for clinical integration and for acquiring both modalities during a single acquisition. Integrating fMRI and MRSI would overcome these constraints.

BRIEF SUMMARY OF THE INVENTION

In one embodiment of the present invention, simultaneous acquisition of multiple MRI contrasts significantly reduces acquisition time, resulting in considerable cost saving. The reduced scan time also enhances patient comfort.

In another embodiment, the present invention concurrently acquires MRSI and fMRI data in the same scan while subjects are either performing tasks to activate brain regions or remain at rest, which allows monitoring of resting state brain activity and connectivity.

In one embodiment, the present invention provides new approaches for concurrent measurement of the tissue water and BOLD-contrast signal changes during MRSI acquisition by integrating spatial and spatial-spectral encoding modules into the water suppression, i.e., immediately after the water-excitation RF pulse and before the application of the dephasing gradients. A binomial spatial-spectral water-excitation RF pulse may be used to provide spatial localization within a 2-D slice or 3-D slab.

In another embodiment, the present invention concurrently acquires MRSI and other MRI modalities, such as diffusion tensor MRI, perfusion MRI or high-resolution structural MRI.

In another embodiment, the present invention makes use of the available water signal after or immediately after excitation before it is suppressed, using spatial gradient encoding.

In another embodiment, the present invention uses a readout module with or without radiofrequency (RF) refocusing pulses that may be inserted between the water excitation RF pulse and the dephasing gradients.

In another embodiment of the present invention, readout modules may be inserted in any of the water suppression modules of a multi-pulse water suppression scheme to encode the water signal spatially.

In another embodiment, the present invention provides a novel approach that allows flexible integration of multiple imaging modalities into the WS module of high-speed MRSI that can be tailored.

In another embodiment, the present invention provides an approach that significantly reduces the acquisition time, and failure rate of volumetric, quantitative MRSI and is compatible with a wide range of spectroscopic acquisition methods.

In another embodiment, the present invention provides a reduced scan time that facilitates integration of 3D high-speed, short TE MRSI into clinical presurgical imaging protocols. The additional integration of fMRI considerably reduces scan times for multi-modal neuroscience research and clinical imaging studies while maintaining MRSI sensitivity and only minor decreases in fMRI sensitivity.

In another embodiment, the present invention provides a combined fPEPSI approach that is suitable for concurrently probing associations between dynamic metabolic or neurotransmitter changes with BOLD signal changes.

BRIEF DESCRIPTION OF THE SEVERAL VIEWS OF THE DRAWINGS

In the drawings, which are not necessarily drawn to scale, like numerals may describe substantially similar components throughout the several views. Like numerals having different letter suffixes may represent different instances of substantially similar components. The drawings illustrate generally, by way of example, but not by way of limitation, a detailed description of certain embodiments discussed in the present document.

FIGS. 6A, 6B, 6C, 6D, 6E, 6F, 6G, and 6H show 3D PEPSI water-suppressed (WS; left) and water reference (WR; right) spectral arrays reconstructed online in 6 of the 8 encoded slices inside the selected slab (TR/TE: 1250/15 ms, 7×7×7 mm3 voxel size, scan time: 2:56 min). (g) Enlarged WS and (h) WR spectral arrays in slice 1. The high-resolution MRIs display the localization of the outer volume suppression slices.

FIGS. 9A, 9B and 9C shows semi-LASER PEPSI with concurrent water reference acquisition in a patient with WHO grade III anaplastic astrocytoma (TR/TE: 1350/36, 0.34 cc voxel, 3:10 min). (a) Metabolite maps, (b) spectrum in central region of the tumor, and (c) spectrum on the contralateral healthy side.

DETAILED DESCRIPTION OF THE INVENTION

Figure 1:
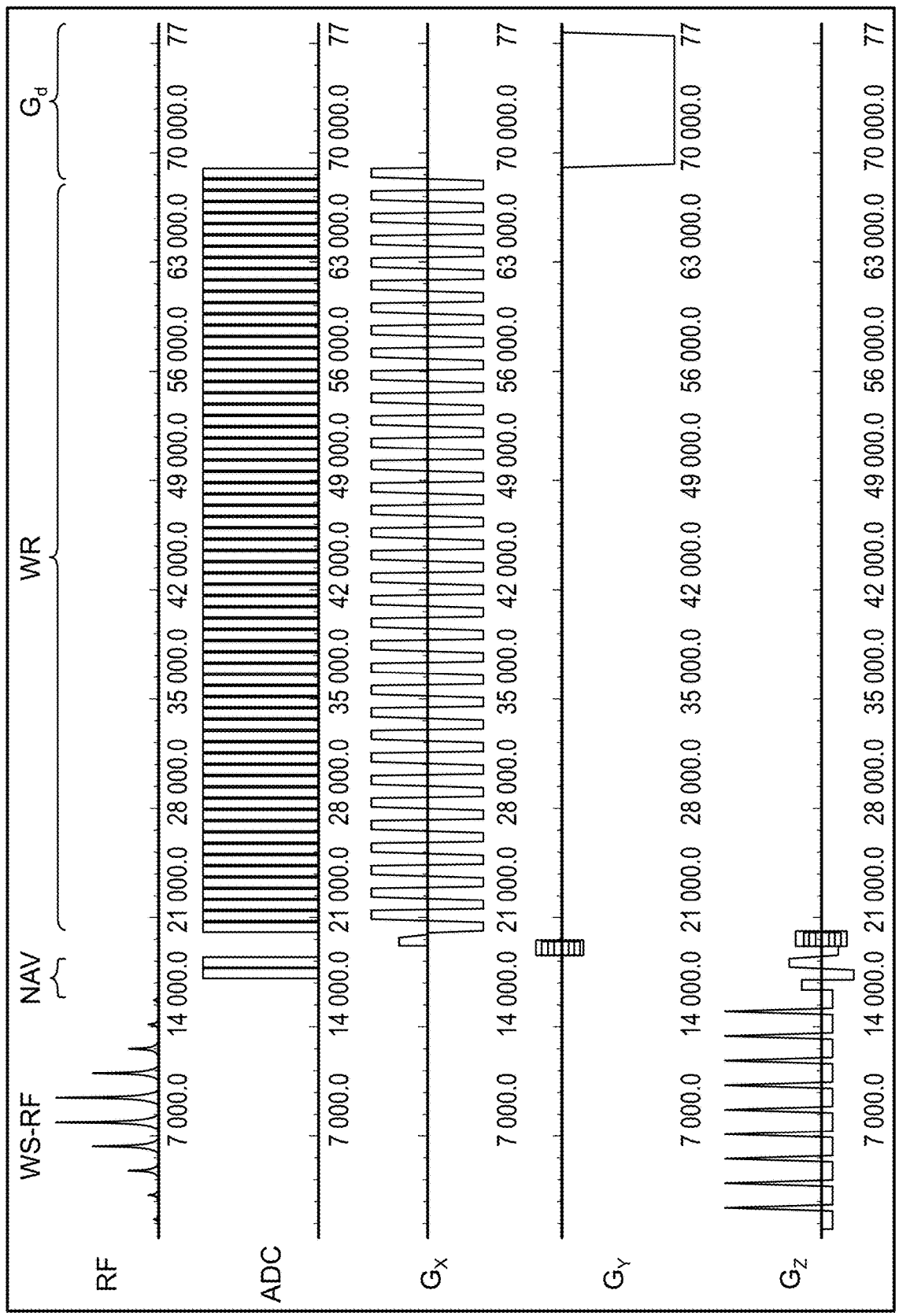
FIG. 1 shows a water suppression module with spatial-spectral echo-planar water reference (WR) acquisition, binomial slab-selective spatial-spectral RF pulse (WS-RF) for excitation, bipolar navigator (NAV) to monitor signal amplitude and phase stability, and dephasing gradient $G_d$ for an embodiment of the present invention.

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a representative basis for teaching one skilled in the art to variously employ the present invention in virtually any appropriately detailed method, structure, or system. Further, the terms and phrases used herein are not intended to be limiting, but rather to provide an understandable description of the invention.

MRSI is typically performed with water suppression to reduce the overwhelming water signal in the proton MR spectrum. The water signal is considered a nuisance signal and discarded often in the water suppression modules. In one embodiment, the present invention makes use of the available water signal after or immediately after excitation before it is suppressed, using spatial gradient encoding. Specifically, a readout module with or without radiofrequency (RF) refocusing pulses may be inserted between the water excitation RF pulse and the dephasing gradients.

Readout modules can be inserted in any of the water suppression modules of a multi-pulse water suppression scheme to encode the water signal spatially. The elongation of the water suppression module(s) due to the insertion of the short readout module is minor. In case outer volume suppression is used, the minimum duration of the water suppression modules is dominated by the duration of the spatial outer volume suppression modules that are inserted into the last water suppression module.

A preferred embodiment of the invention uses a spatial-spectral water excitation RF pulse that pre-localizes the water signal within a slice or a slab. The excited water signal can be mapped using the following methods (a) 1D spatial encoding with phase encoding in one or two dimensions, (b) 2D single-shot spatial encoding with or without phase encoding in one dimension or (c) 3D single-shot spatial encoding. Image encoding can be accelerated with established k-space undersampling methods, including parallel imaging, such as GRAPPA and SENSE, and compressed sensing to achieve higher spatial and/or temporal resolution.

The insertion of multiple spatial-spectral and/or spatial encoding modules into the water suppression modules enables encoding a multitude of MRI contrasts concurrently with the water-suppressed spectroscopic image. Examples include blood-oxygenation-level-dependent contrast, high-resolution proton-density and $T_2$-weighted contrast, and diffusion tensor contrast. The acquisition of serial images enables mapping of blood-oxygenation-level-dependent signal changes during changes in brain activation, to map brain function concurrently with mapping metabolites.

Embedding encoding modules into the water suppression modules results in an SNR penalty compared with a conventional MRI sequence due to (a) the short encoding duration of the embedded encoding module ($T_{emb}$) relative to TR, which can be as large as $$\sqrt{Temb/TR}$$

depending on the acquisition duty cycle of the conventional MRI sequence, and (b) the amplitude of the residual water signal in a given water suppression module. Further, the spatial uniformity of the signal may vary depending on the spatial uniformity of the water excitation RF pulse and the residual water signal in a given water suppression module, which depends on $B_0$ and $B_1$ inhomogeneity in the volume of interest. As a consequence, acquisitions that require high signal intensity and/or high image intensity uniformity (e.g. a water reference or high-resolution MRI scan) are preferably collected using the first water suppression module.

Figure 3:
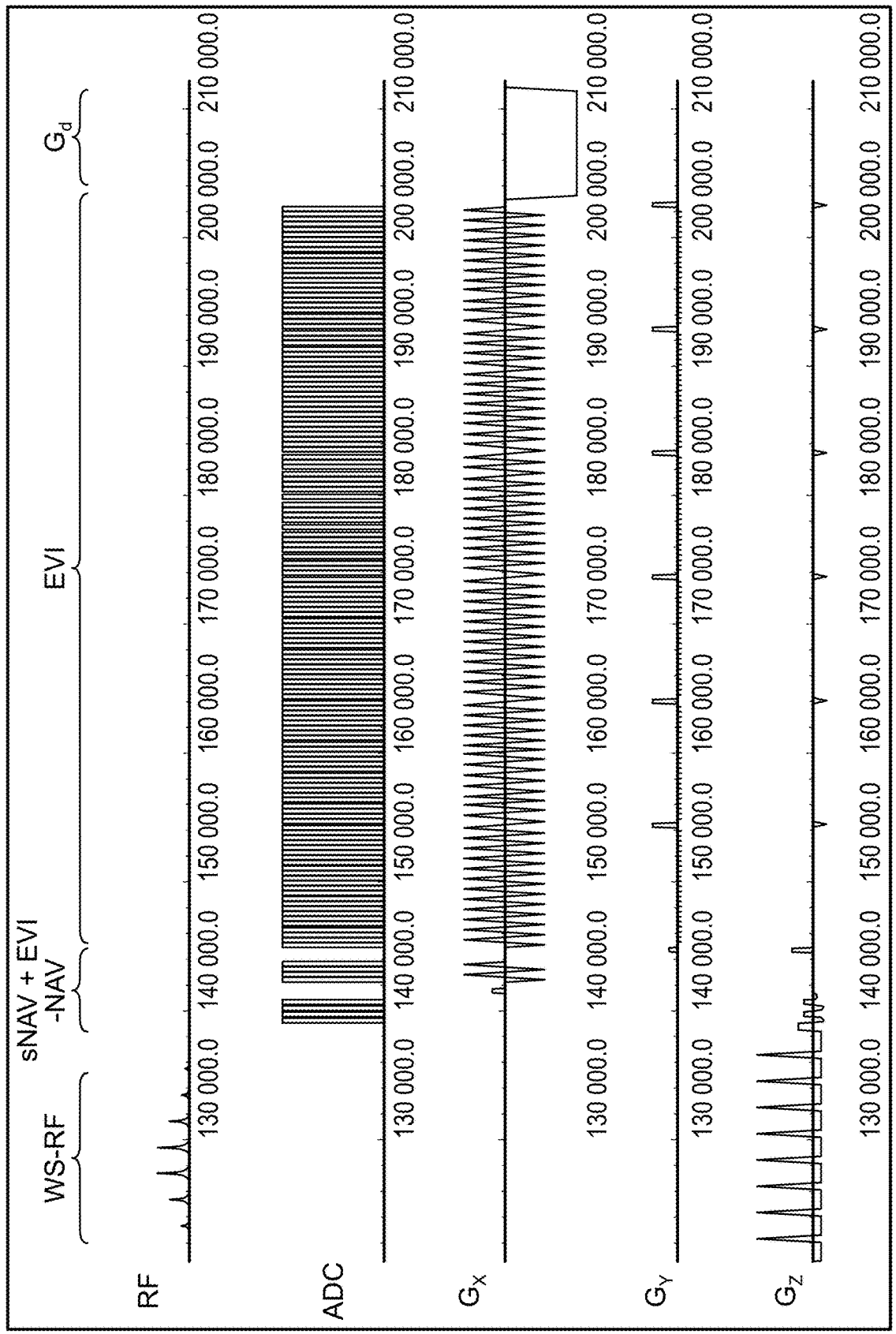
FIG. 3 shows a water suppression module with echo-volumar imaging (EVI) readout module, binomial slab-selective spatial-spectral water suppression RF pulse (WS-RF), slice-selective navigators (sNAV), EVI ghost correction navigators (EVI-NAV), EVI readout and dephasing gradient ($G_d$) for an embodiment of the present invention.
Figure 4A:
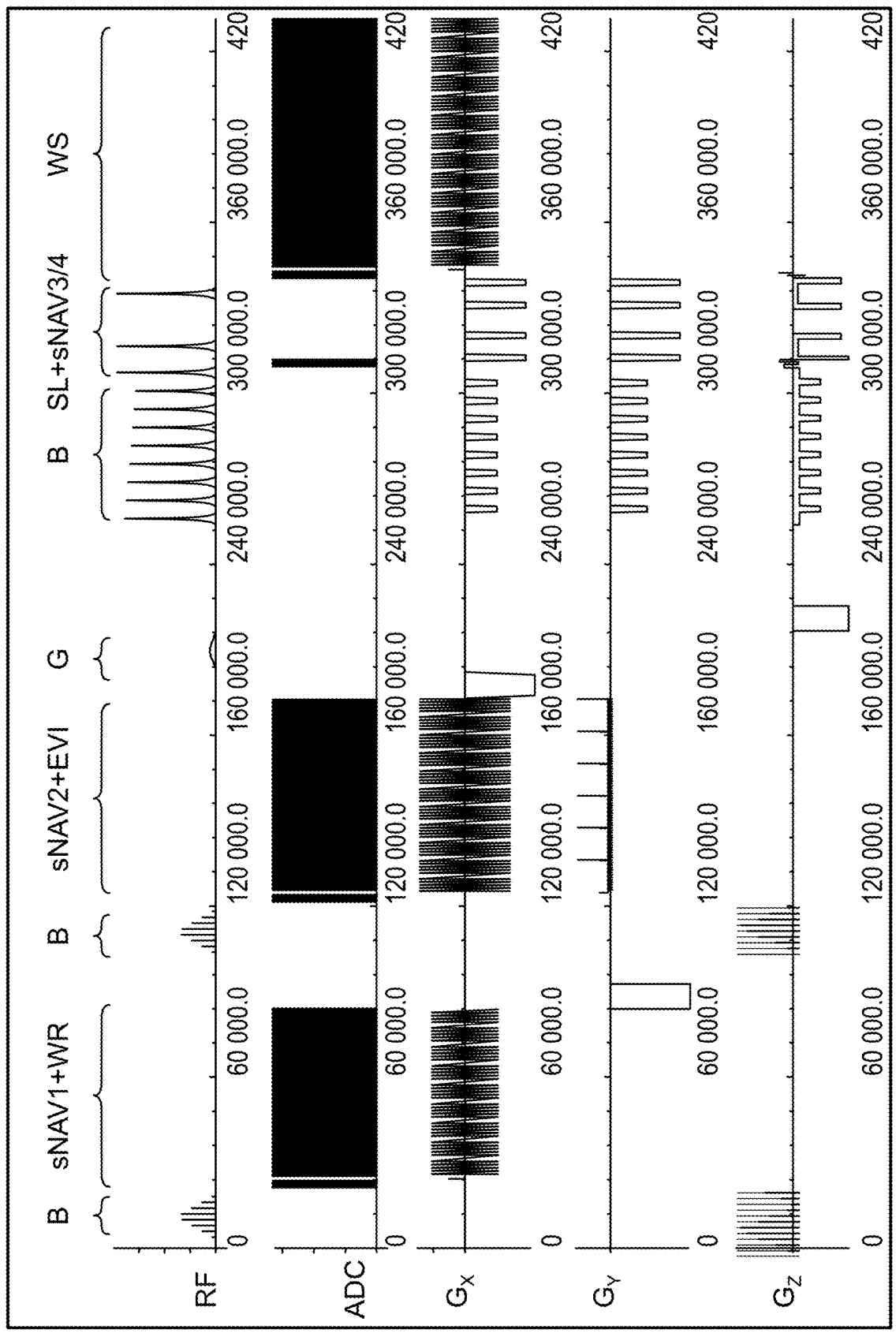
FIGS. 4A and 4B show a PEPSI pulse sequence with water reference acquisition (WR) and echo-volumar imaging (EVI) module integrated into the water suppression. (a) WR in water suppression module 1 and EVI in in water suppression module 2. (b) WR1 and EVI in water suppression module 1 and WR2 in in water suppression module 2. Binomial slab-selective spatial-spectral (B) and Gaussian (G) water suppression RF pulses, 4 slice-selective navigators (sNAV1-4), outer volume suppression (OVS), semi-LASER slab selection (sL), and water-suppressed readout (WS).

A hybrid proton-echo-planar-spectroscopic-imaging (PEPSI) pulse sequence with concurrent acquisition of a water reference spectroscopic image using the first water suppression module, a volumetric fMRI scan in each of the second water suppression modules and a water-suppressed spectroscopic image was developed on a Siemens Trio 3 Tesla MRI scanner (operating system version: VB17A). The pulse sequence diagram is shown in FIG. 4A. Binomial spatial-spectral water excitation RF pulses are used to pre-localizes the water signal within a slab. FIG. 3 shows the second water suppression module with the embedded single-shot echo-volumar-imaging (EVI) module with binomial excitation RF pulse and navigator acquisition modules.

Figure 7:
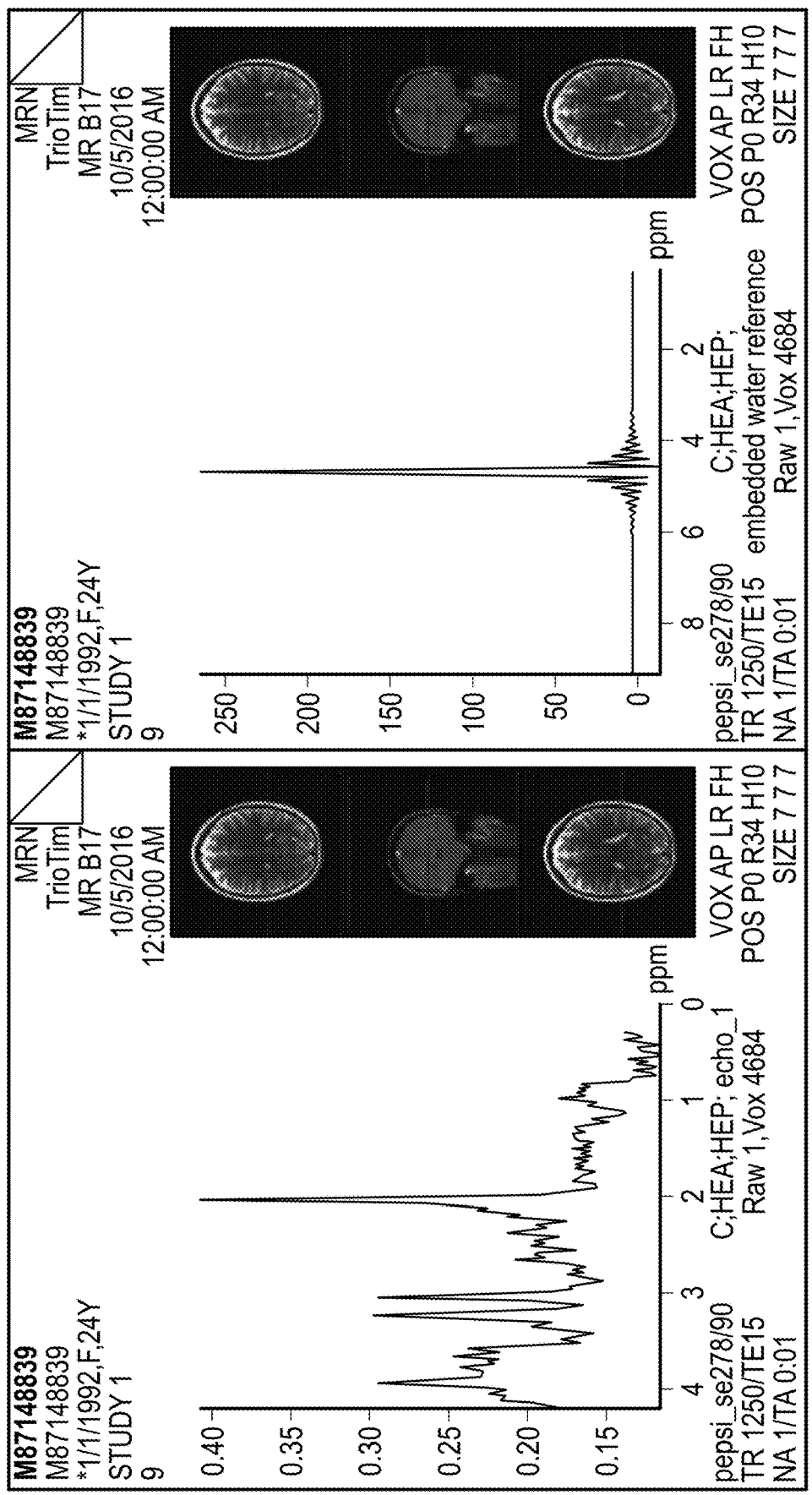
FIG. 7 shows online reconstructed (left) water-suppressed and (right) water reference spectra from a white matter voxel in slice 5 of the data shown in FIG. 2.
Figure 10A:
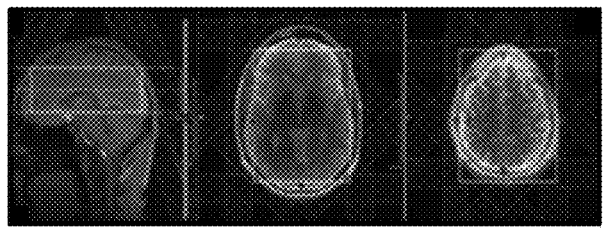
FIGS. 10A, 10B, 10C, 10D, 10E, 10F, 10G, 10H, 10I, 10J, 10K and 10L show simultaneous fMRI and MRSI using semi-Laser fPEPSI with integrated EVI and water reference acquisition modules. (a-f) EVI without GRAPPA acceleration inside the 2nd water suppression module (PEPSI TR/TE: 1160/38.5 ms, voxel size: 4×4×7 mm3, EVI: TR/TE: 1160/50 ms, voxel size: 4×8×7 mm3, total scan time: 5:26 min). Simultaneous visual stimulation and bilateral motor task. (a) Slab localization with outer volume suppression slices. (b) Visual activation. (c) Motor activation. (d) Metabolite maps of Cho, Cr, and NAA. (e) Water-suppressed spectrum with LCModel fit in white matter and (f) corresponding water reference spectrum. (g-l) EVI with 4-fold GRAPPA acceleration inside the 1st water suppression module (TR/TE: 1500/38.5 and 1500/39 ms for PEPSI and EVI, respectively, voxel size: 4×4×6 mm3, total scan time: 7:02 min). (g-i) Sequential visual stimulation (3 min) and resting-state (4 min) experiments using slab localization encompassing occipital cortex (g) Visual activation map and (h) corresponding raw data time course. (i) Visual resting-state network. (j-l) Sequential bilateral finger tapping (3 min) and resting-state (4 min) experiments using the same pulse sequence as in (g-i) with slab localization encompassing motor cortex. (j) Sensorimotor activation map and (k) corresponding raw data time course in left motor cortex. (l) Sensorimotor resting-state network.
Figure 10B:
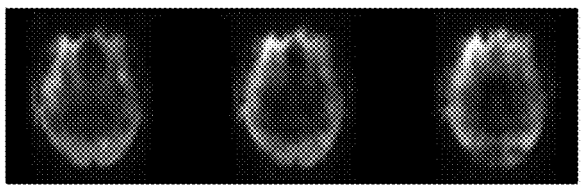
Figure 10C:
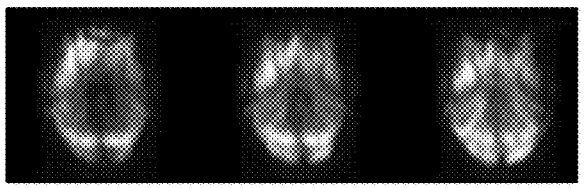
Figure 10D:
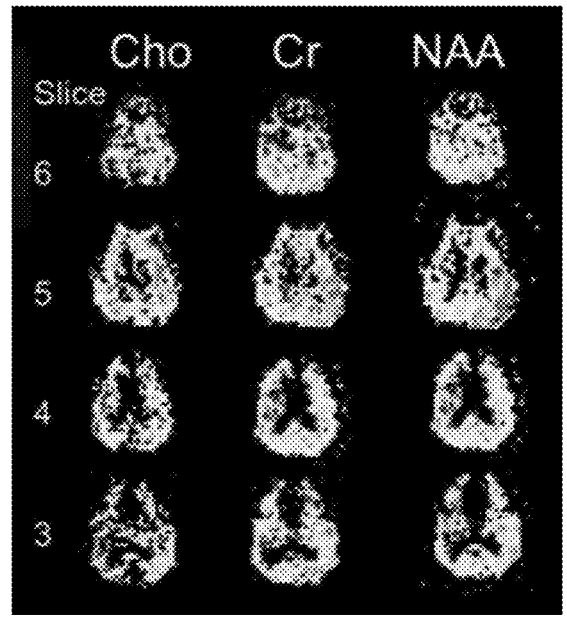
Figure 10E:
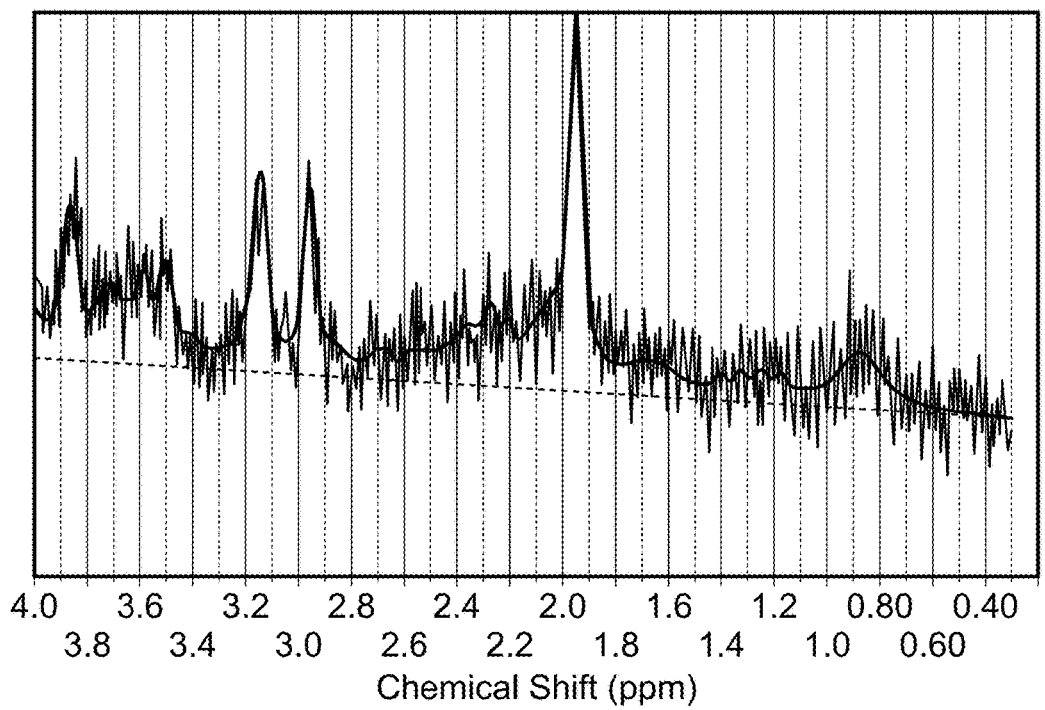
Figure 10F:
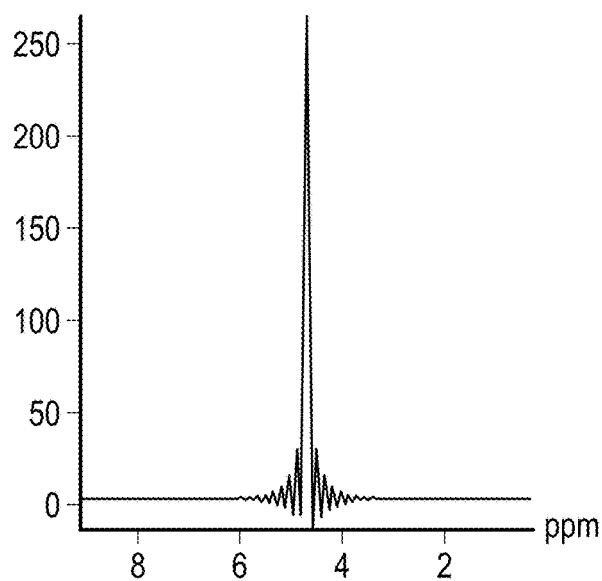
Figure 10H:
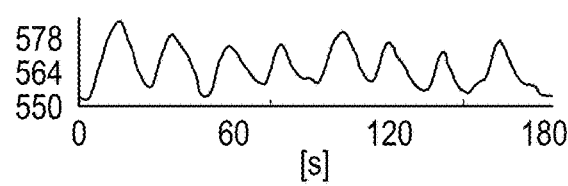

In vivo data in healthy controls were acquired on a Siemens Trio 3 Tesla MRI scanner using a 32 channel head array RF coil. A sensori-motor fMRI experiment was concurrently conducted during the MRSI acquisition. The block design paradigm consisted of 8 repetitions of simultaneous finger tapping and eyes open (8 seconds) versus rest and eyes closed (12 seconds). Water reference and water suppressed data were acquired using either TR/TE=1250/15 ms, 32×32×8 spatial matrix, 7×7×7 mm³ voxel size and 3 min scan time or TR/TE=1160/38.5 ms, 64×64×8 spatial matrix, 4×4×7 mm³ voxel size and 5:26 min scan time. Water reference and water suppressed data reconstructed online as described previously. Embedded EVI data ($TE_{eff}$=35 ms) were acquired at every TR using either 3.5×7×7 mm³ voxel size and 64×24×6 raw data matrix or 7×7×7 mm³ voxel size and 32×24×6 raw data matrix. Both $k_y$ and $k_z$ were encoded using 6/8 partial Fourier acquisition. The duration of the EVI encoding module was 63 ms. EVI data were extracted from the raw data and reconstructed offline using zero-filling of the $k_y$ and $k_z$ dimensions into a 64×64×8 or 32×32×8 spatial matrix using custom software routines written in MATLAB. Model-based, seed-based and data-driven fMRI analysis of the reconstructed EVI data was performed using the Turbo-FIRE fMRI analysis software[4] and GIFT ICA analysis software tools (http://mialab.mrn.org/software/gift/). Examples of concurrently acquired and online reconstructed metabolite and water reference spectra using this hybrid PEPSI sequence are shown in FIG. 7. FIGS. 10a and 10b shows reconstructed EVI images showed brain activation in visual and motor cortex as well as resting state connectivity in major resting state networks.

Figure 2:
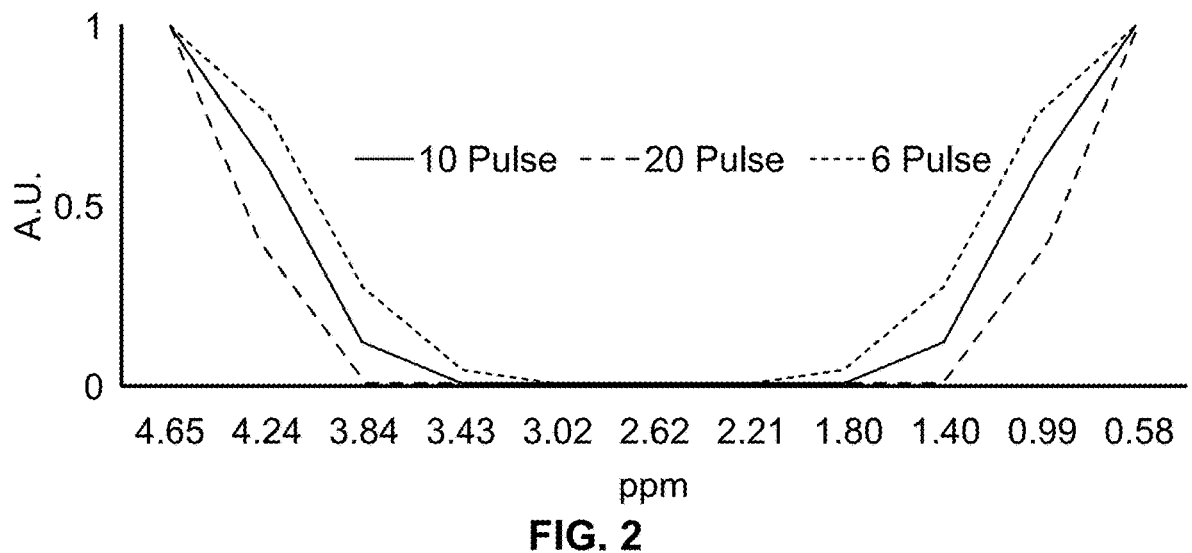
FIG. 2 shows frequency selectivity of binomial water-excitation RF pulses with different number of sub-pulses for an embodiment of the present invention.

In yet other embodiments, the present invention concerns WR acquisition that consists of a binomial RF pulse, a short navigator with a bipolar readout gradient along the slice direction to monitor water phase and frequency changes, conventional phase encoding along $k_y$ and $k_z$, and a spatial-spectral encoding module using a train of echo-planar readout gradients. The spatial-spectral encoding module was shorter in duration (128 gradients vs. 2048 gradients) but was otherwise identical to the echo-planar spatial-spectral encoding module for metabolite signals as shown in FIG. 1. A binomial RF pulse, offers flexibility in spectral selectivity with tolerance to $B_0$ inhomogeneity, was chosen for slab and spectrally selective water suppression. A simulation of the excitation profile (FIG. 2) showed that a 10 RF sub-pulse monopolar design with 2 ms inter-pulse spacing provides an acceptable compromise between the non-excitation spectral range (<0.5% suppression between 1.8 and 3.43 ppm) to encompass all metabolites of interest at 3T (including Inositol, Lactate and the 1.3 ppm Lipid peak), $B_0$ offset tolerance, water suppression bandwidth (full width at half maximum (FWHM): 116 Hz) and RF pulse duration (21 ms).

The EVI module using repeated EPI modules with interleaved $k_z$ phase encoding gradients for this embodiment is shown in FIG. 3. Two navigator signals were acquired before the first EPI module using a bipolar readout gradient. The EPI modules consisted of trapezoidal gradients ($G_{RO}$) along the readout direction and a series of blipped primary phase encoding gradients ($G_{PE1}$) that were rewound at the end of every partition. A blipped secondary phase encoding gradient ($G_{PE2}$) encodes the third spatial dimension and may be applied after each EPI module. $K_y$ and $K_z$, -space was either fully sampled or encoded asymmetrically with 6/8 partial Fourier acquisition using a dephasing gradient before the first EPI module ($k_{max/2}$) The $k_y$ and $k_z$, space trajectories for each $k_z$ step were traversed in the same direction using either full sampling or 4-fold acceleration for GRAPPA reconstruction. Sixteen GRAPPA auto-calibration signal (ACS) lines for in-plane GeneRalized Autocalibrating Partial Parallel Acquisition (GRAPPA) reconstruction using the same pulse sequence with segmented EPI acquisition were measured in a separate prescan. Multiple-slab EVI encoding in consecutive TRs of the MRSI acquisition were also supported.

Figure 4B:
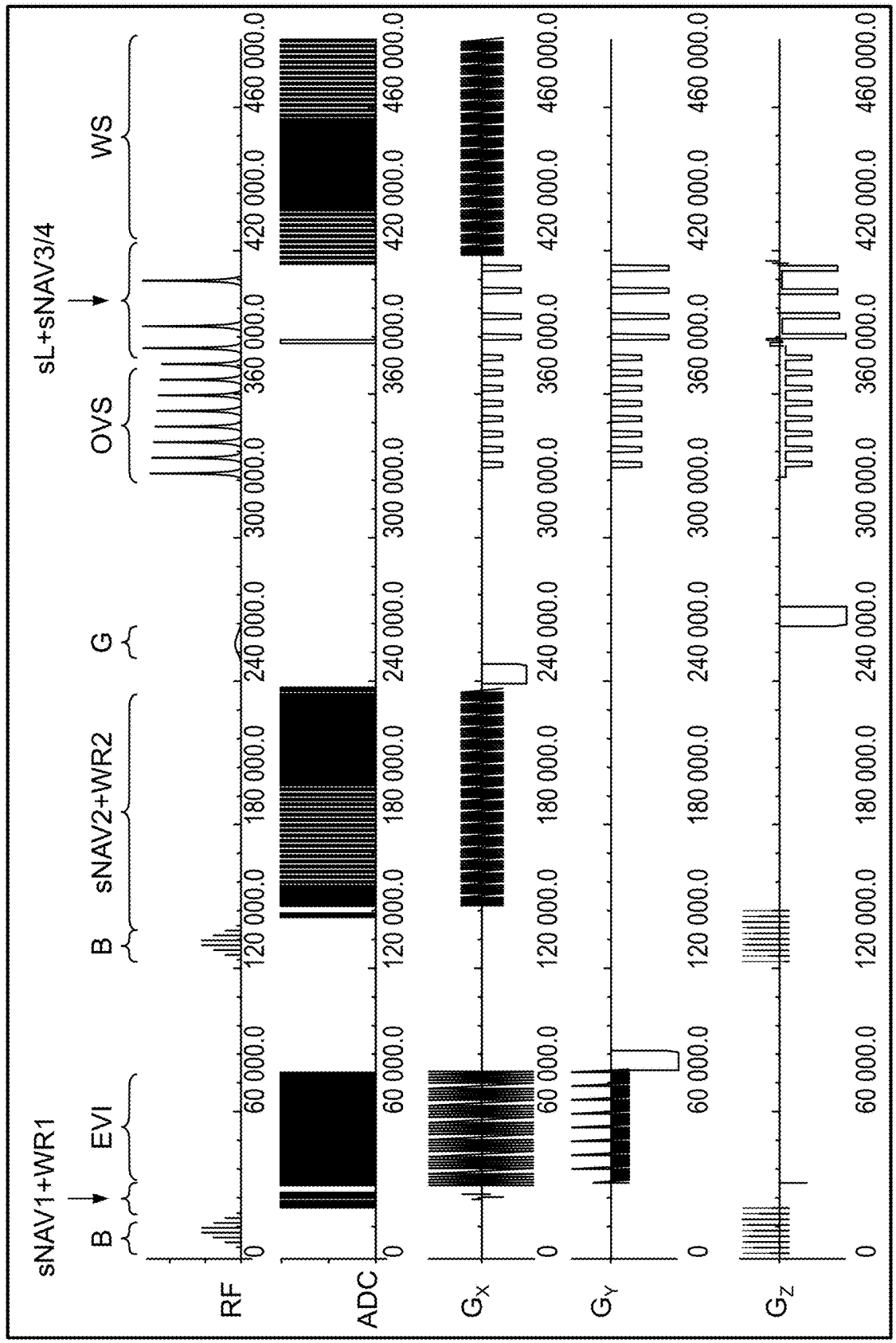

For concurrent acquisition of WS and WR data, the spatial-spectral echo-planar WR acquisition was integrated into the first WS module of a 3-pulse WET water suppression sequence. For concurrent acquisition of WS, WR and fMRI data, the EVI module was initially integrated into the second WS module of the 3-pulse WET WS sequence as shown in FIG. 4a. In the first subsequent implementation of concurrent fMRI and MRSI, the WR acquisition in the first WS module was shortened to a bipolar readout gradient and the EVI module was moved from the second to the first WS module, immediately behind the shortened WR acquisition. A second longer WR data acquisition module was integrated into the second WS module to enable eddy current correction as shown in FIG. 4b.

Figure 5:
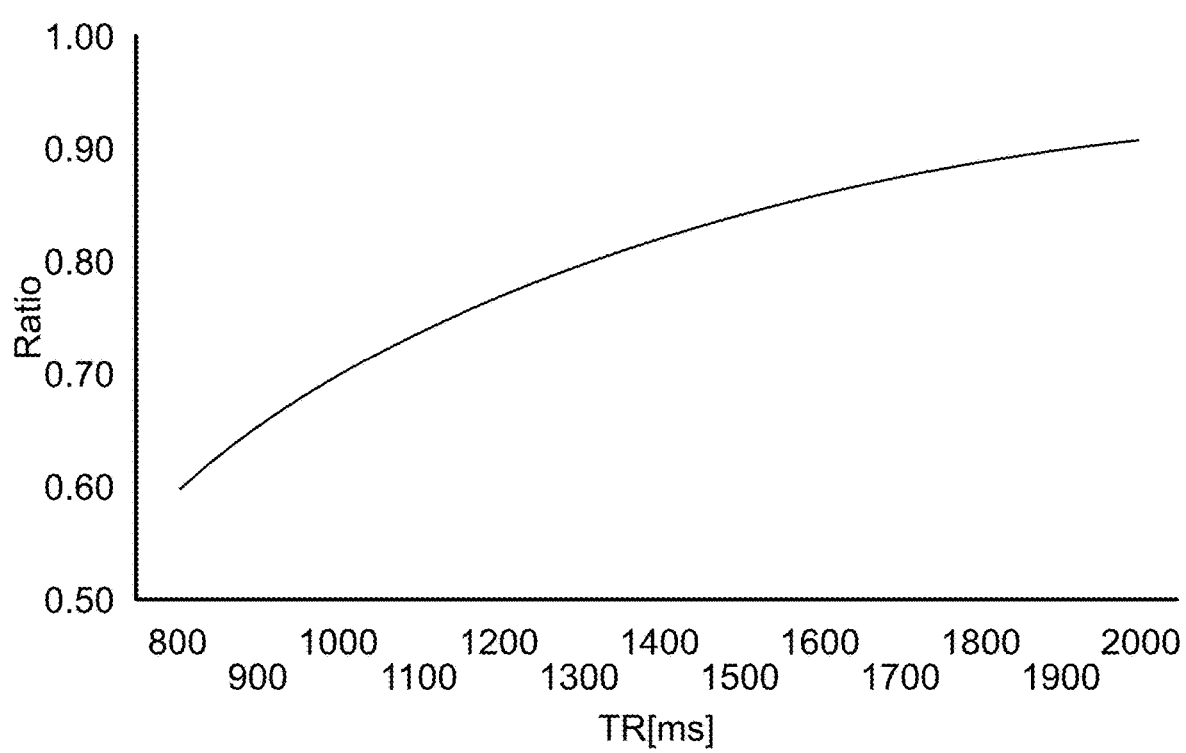
FIG. 5 illustrates relative signal intensity of fMRI in concurrent fMRI/MRSI acquired with 89.20 degree water suppression flip angle relative to conventional fMRI acquired with Ernst angle as a function of TR for an embodiment of the present invention.

This approach of concurrent fMRI and MRSI with integration of MS-EVI into the first WS module of PEPSI reduces fMRI signal intensity compared with conventional fMRI, since a flip angle close to 90 degrees is required for optimal water suppression and the water saturation recovery period is reduced by the duration of the WS module. The steady-state signal amplitude of this fPEPSI approach relative to conventional fMRI is therefore:

$$R_{fPEPSI/fMRI} = \frac{(1-e^{-TR/T_1})\sin\alpha_{Ernst}(1-\cos\alpha_{WS}e^{-(TR-T_{WS})/T_1})}{(1-\cos\alpha_{Ernst}e^{-TR/T_1})(1-e^{-(TR-T_{WS})/T_1})\sin\alpha_{WS}} \qquad \text{Eq. 1}$$

where $\alpha_{Ernst}$ is the Ernst angle, $\alpha_{WS}$ is the flip angle of the first WET WS-RF pulse (89.2 degrees) and $T_{WS}$ is the duration of the WET sequence. A simulation of the fMRI signal amplitude in fPEPSI relative to conventional fMRI as a function of TR is shown in FIG. 5.

Data were acquired on clinical 3T Siemens Trio scanners equipped with 12 and 32 channel array coils. Seven healthy adults (4F, 3M, 24-59 yrs), a 3-month old infant (M) and a patient (F) with world health organization (WHO) grade III anaplastic astrocytoma were scanned using PEPSI with concurrent WR acquisition. Four healthy adults (1F, 3M, 19-57 yrs) were scanned using PEPSI with concurrent fMRI and WR acquisition.

Three different pulse sequence versions and parameter settings, with manually prescribed 8-slice OVS, were used: (1) 2D PEPSI with integrated WR acquisition was performed with slice-selective spin-echo excitation or PRESS prelocalization using cardiac gating and: TR/TE: 2000/90 ms, spatial matrix: 32×32, FOV: 320 or 480 mm, slice thickness: 2 cm, nominal voxel size: 1×1×2 cc or 1.5×1.5×2 cc spectral width: 1087 Hz, number of spectral points (WS/WR): 1024/64, digital spectral resolution: 1 Hz (metabolites) and 16 Hz (water), and scan time: 64 s using single signal average. (2) 3D PEPSI with integrated WR acquisition was performed with slab-selective spin-echo excitation (TR/TE: 1250/15 ms) or semi-LASER slab-selective double spin-echo excitation with adiabatic refocusing RF pulses (TR/TE: 1320/32-36 ms) using spatial matrix: 32×32×8, elliptical sampling, in-plane FOV: 224 mm, slab FOV: 56 mm, slab thickness: 42 mm, nominal voxel size: 7×7×7 mm³ (0.34 cc), spectral width: 1087 Hz, number of spectral points (WS/WR): 1024/128, digital spectral resolution: 1 Hz (metabolites) and 8 Hz (water), scan time using single signal average: 2:56 or 3:08 min depending on TR. (3) Semi-LASER 3D PEPSI with integrated EVI and WR acquisition (fPEPSI, as discussed below) was performed using: TR/TE: 1160/38.5 ms or 1500/38.5 ms, spatial matrix: 64×64×8, elliptical sampling, in-plane FOV: 256 mm, slab FOV: 48 or 56 mm, slab thickness: 36 or 42 mm, nominal voxel size: 4×4×6 mm³ (0.096 cc) or 4×4×7 mm³ (0.112 cc), spectral width: 735 Hz, digital spectral resolution: 1.4 Hz (metabolites) and 12 Hz (water), scan time using single signal average: 5:26 or 7:02 min, depending on TR.

Two different pulse sequence versions and parameter settings were used concurrently during high spatial resolution (64×64×8) PEPSI acquisitions: (1) Semi-LASER 3D fPEPSI with EVI inside the second WS module: TR/TE: 1160/50 ms, partial $k_y$ and $k_z$ acquisition (without using GRAPPA acceleration) with raw data matrix: 64×24×6, voxel size: 4×8×7 mm³, and scan time: 5:26 min. A simultaneous block-design motor-visual task (8 seconds of 2 Hz index finger tapping and eyes open vs. 12 seconds of rest with eyes closed) was performed. (2) Semi-LASER 3D fPEPSI with EVI inside the first WS module using 4-fold GRAPPA acceleration: TR/TE: 1500/39 ms, partial $k_y$ and $k_z$ acquisition with 4-fold undersampling along $k_y$ and raw data matrix: 64×12×6, voxel size: 4×4×6 mm³, and scan time: 7:02 min. ACS data were acquired in a short prescan using the same pulse sequence with segmented EPI acquisition and without using $k_y$ encoding in the PEPSI acquisition. A 3-minute block-design task (8 seconds of 2 Hz index finger tapping or eyes open vs. 12 seconds of rest with eyes closed) followed by 4 minutes of resting-state (eyes open with fixation of a cross-hair) was performed.

WR and WS data were reconstructed online in the image calculation environment (ICE) using re-gridding to correct ramp sampling, separate spatial-spectral reconstruction of even-echo and odd-echo data, navigator-based phase correction and combination of even-echo and odd-echo data as described previously. WR data were zero-filled to the same number of data points (1024) as the WS data. Spectral quantification of WS data in reference to tissue water was performed using LCModel fitting with simulated basis sets containing 18 metabolites. mLCModel fitting of the WR data was performed using a truncated and edited singlet (N-acetyl-aspartate (NAA) or choline (Cho)) basis set that was line-shape matched to the WR data by applying a boxcar filter in the time domain to shorten the signal to match the duration of the WR data. The results were scaled to account for the difference in protons in the edited basis set and water. Ratio images of metabolite/water were computed and corrections for water content and water age-specific signal relaxation correction were applied as described in our recent study. The following thresholds were applied: Cramer-Rao Lower Bounds (CRLBs)<20% for singlets, Inositol, and Glutamate/Glutamine (Glx), and <40% for lower concentration multiplets; linewidth <0.08 ppm, SNR >2. For 3D data, the results were averaged across the 4 central slices. Correction was additionally applied for water content, partial volume effects, and tissue-specific water and metabolite relaxation times in one subject to compute fully quantitative metabolite levels in gray and white matter tissues.

Single and multi-slab EVI data were reconstructed offline using MATLAB routines. The reconstruction pipeline extracted the fMRI data segments from the raw data file and applied regridding to correct ramp sampling. Partial Fourier data were zero-filled and navigator-based phase correction was applied. GRAPPA reconstruction was performed based on the ACS data acquired in the prescan. Final data matrix size was 64×64×8. Model-based and seed-based fMRI analyses of the reconstructed EVI data were performed using the TurboFIRE. Preprocessing included motion correction, spatial smoothing of fMRI analysis software tool raw images using a 5 mm³ Gaussian spatial filter, and 8 s moving average time domain low pass filter with a 100% Hamming window width to reduce signal fluctuations due to cardiac and respiratory pulsations. Task-based fMRI data were processed using model-based correlation analysis with a reference vector that was convolved with a canonical hemodynamic response function. Resting-state fMRI data were processed using seed-based, moving average sliding-window (15 s width) correlational analysis with regression of motion parameters and signals from white matter and cerebrospinal fluid. Cluster analysis was applied to compute the spatial extent (number of voxels), peak and mean correlation of the activation and connectivity maps.

Figure 8A:
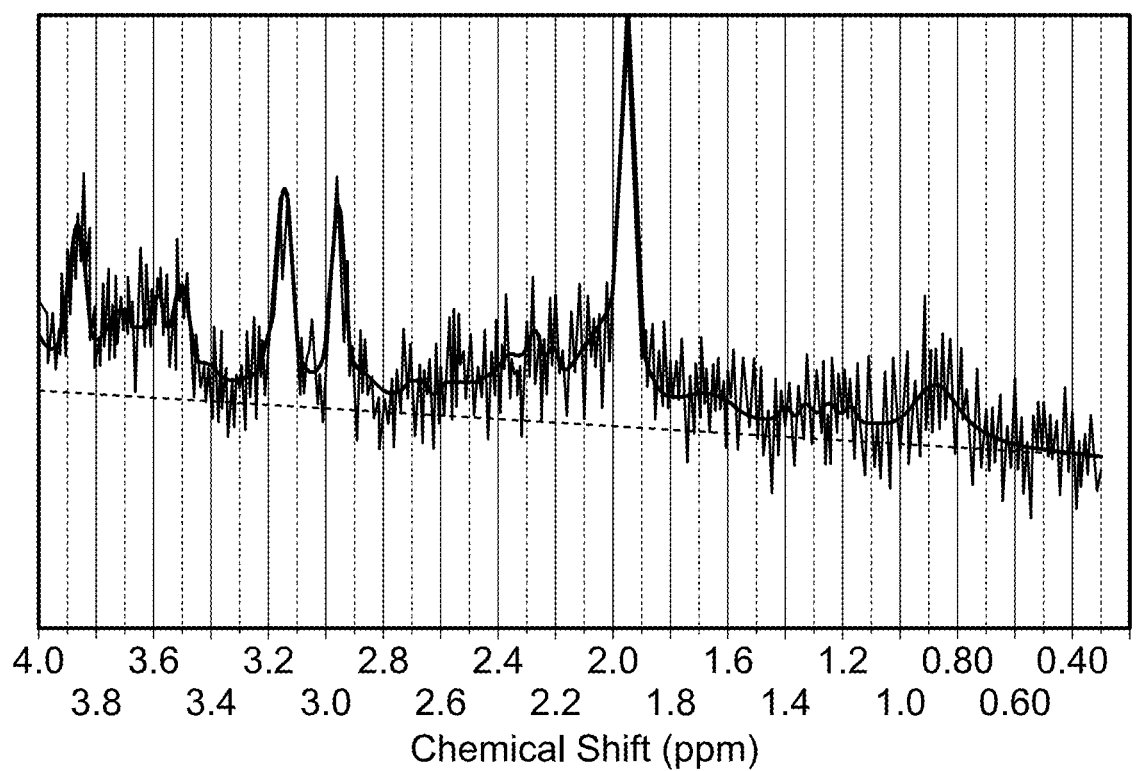
FIGS. 8A and 8B are the CModel fit of (a) water-suppressed and (b) water reference spectra from a white matter voxel in slice 5 of the data shown in FIG. 3.
Figure 8B:
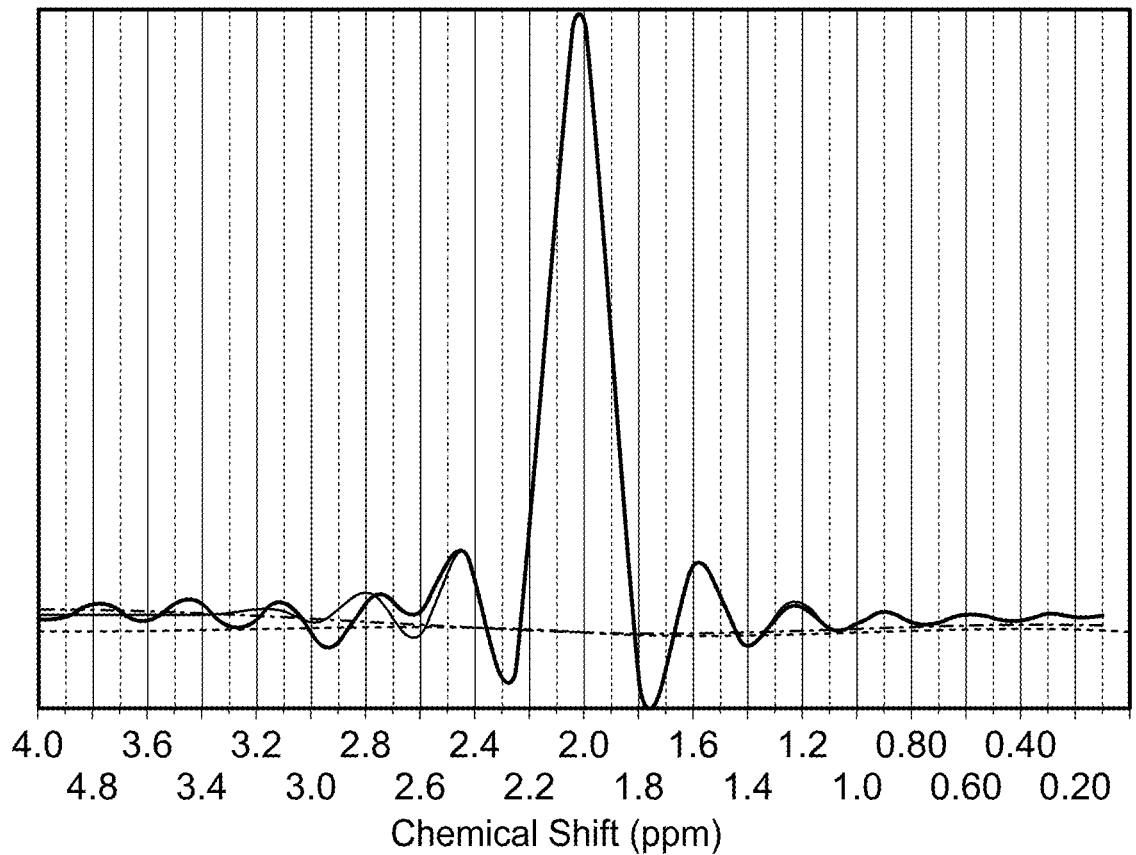

Integration of the WR and EVI acquisition into the PEPSI pulse sequence with OVS prolongated minimum TR by less than 50 ms. The integration of these modules had negligible impact on SNR and water suppression efficiency. The spectral quality (i.e., line-shape and width, baseline distortion, and lipid contamination) of 3D short TE PEPSI data acquired with integrated WR acquisition, 32×32×8 matrix size, 7×7×7 mm³ voxel size and 3 min scan time were comparable to conventional PEPSI data as shown in FIGS. 6 and 7. LCModel fitting results of both WS and WR data were consistent with conventional water-suppressed and non-water-suppressed PEPSI data as shown in FIG. 8. Metabolite concentration values were in the range of previous studies (Table 1a) with Cramer-Rao lower bounds ranging from 8.6-13.6 on average across subjects for major singlets, to 16.4 for Glu+Gln (Table 1b).

| Subject: | 1 | 2 | 3 | 4 | 5 | Mean | SD |
|---|---|---|---|---|---|---|---|
| Cho | 1.7 | 1.9 | 1.7 | 1.8 | 1.8 | 1.8 | 0.1 |
| Cr + PCr | 5.8 | 7.1 | 5.4 | 6.4 | 6.0 | 6.1 | 0.6 |
| Glu + Gln | 12.3 | 11.2 | 10.4 | 10.8 | 13.5 | 11.7 | 1.1 |
| NAA + NAAG | 10.8 | 10.8 | 10.5 | 10.5 | 10.1 | 10.5 | 0.3 |
| SNR | 5.6 | 5.0 | 4.3 | 5.2 | 5.1 | 5.0 | 0.4 |
| FWHM [Hz] | 0.046 | 0.053 | 0.049 | 0.050 | 0.054 | 0.050 | 0.003 |

Table 1a: Volume-averaged metabolite concentrations, FWHM and SNR and (b) Cramer-Rao lower bounds in short TE 3D PEPSI in 5 healthy controls.

| Subject: | 1 | 2 | 3 | 4 | 5 | Mean | SD |
|---|---|---|---|---|---|---|---|
| Cho | 14.1 | 12.5 | 13.7 | 13.5 | 14.0 | 13.6 | 0.6 |
| Cr + PCr | 11.5 | 9.2 | 12.5 | 10.8 | 10.7 | 10.9 | 1.1 |
| Glu + Gln | 15.5 | 16.1 | 17.9 | 18.1 | 14.2 | 16.4 | 1.5 |
| NAA + NAAG | 8.6 | 7.9 | 9.0 | 8.8 | 8.6 | 8.6 | 0.4 |

Table 1b: Volume-averaged Cramer-Rao lower bounds in short TE 3D PEPSI in 5 healthy controls.

The SNR ranged from 4 in central voxels to 7 in lateral voxels, reflecting the sensitivity profile of the 32-channel array coil. The average SNR across voxels and subjects was 5. The FWHM varied between 0.04 and 0.06 ppm, depending on slice position, and was 0.05 ppm on average across subjects. Inter-subject variability reflects in part differences in slab location and angulation. Metabolite concentration values in white and gray matter, which were computed in one of the subjects using partial volume and tissue-specific relaxation correction (Table 2), were found to be within the range of a prior study.

| | WM | | GM | | Slope | |
|---|---|---|---|---|---|---|
| | Mean | SD | Mean | SD | Mean | SD |
| | Mean | SD | Mean | SD | Mean | SD |
| | [mmol] | | [mmol] | | [mmol]/% GM | |
| Cho | 1.6 | 0.3 | 1.4 | 0.2 | −0.002 | 0.004 |
| Cr + PCr | 5.5 | 0.9 | 7.5 | 0.5 | 0.021 | 0.005 |
| Glu + Gln | 6.9 | 0.6 | 12.6 | 0.8 | 0.057 | 0.013 |
| NAA + NAAG | 9.1 | 0.8 | 10.2 | 1.1 | 0.012 | 0.017 |

Table 2: Metabolite concentration values in healthy control 1 after partial volume and relaxation corrections, averaged across slices.

Metabolite concentration values measured with single-slice 2D PEPSI at long TE, using either spin-echo slice/slab selection or PRESS prelocalization, were also in the range of results published in previous studies as shown in Table 3.

| Subject | Age/Gender | Pre-Localization | Slice/slab location | Voxel size [mm] | tCho | Cr + PCr | Glu + Gln | NAA + NAAG |
|---|---|---|---|---|---|---|---|---|
| | | | | | Concentration [mmol] (CRLB [%]) | | | |
| 1 | 59 y/M | Slice | peri-ventricular | 10 × 10 × 20 | 1.4 (7.6) | 7.5 (7.4) | 6.8 (16.5) | 8.1 (4.8) |
| 2 | 58 y/M | PRESS | supra-ventricular | 15 × 15 × 20 | 1.8 (7.8) | 7.2 (8.1) | 5.4 (22.4) | 8.3 (4.8) |
| 3 | 17 y/M | PRESS | supra-ventricular | 15 × 15 × 20 | 1.4 (9.8) | 6.3 (8.1) | N/A | 8.8 (5.6) |
| 4 | 3 mo/M | PRESS | supra-ventricular | 15 × 15 × 20 | 1.5 (6.6) | 5 (7.55) | 6.2 (15.3) | 7.5 (6.2) |

Table 3: Slice-averaged metabolite concentrations and Cramer-Rao lower bounds in long TE 2D PEPSI using single-spin-echo and PRESS prelocalization with cardiac gating (TR/TE: 2000/90 ms, scan duration: 1:06 s).

Slice-averaged Cramer-Rao lower bounds in these single-slice 2D PEPSI scans were less than 11% for major singlet resonances (Table 3). The PRESS and spin-echo pre-localized 2D-PEPSI data were affected by differential chemical shift displacement between the 90 degrees and 180 degrees since RF pulses that introduced chemical shift dependent signal attenuation in the frequency range of Glu+Gln and NAA, thus, may help to explain lower Glu+Gln and NAA concentrations in the 2D PEPSI adult data sets compared with the 3D short TE PEPSI data. Regional differences in relaxation times and volume fraction of gray matter, not accounted for in the analyses, may also have contributed to the apparent differences in metabolite concentration measured in 2D and 3D PEPSI. The 2D PEPSI concentration values of Cr+PCr and NAA+NAAG in the infant were reduced compared to 2D PEPSI adult values, which is expected based on previous studies.

Metabolite maps acquired using Semi-LASER PEPSI with concurrent WR (TR/TE: 1350/36, 0.34 cc voxel, 3:10 min) in the patient with WHO grade III anaplastic astrocytoma show an unusual spectral profile with elevated Inositol and Creatine and decreased NAA in the tumor, but only minor elevation of Choline as shown in FIG. 9. The effect of this spectral profile is not apparent in the Cho/NAA map, which displays focal enhancement in central regions of the tumor.

Concurrent fMRI and MRSI in fPEPSI showed clearly detectable task activation signal changes and resting-state connectivity. The initial implementation of EVI into the second WS module using the residual water signal enabled detection of visual and motor activation, albeit at reduced signal intensity and image uniformity compared with conventional fMRI as shown in FIGS. 6a-c. The corresponding WS and WR data were acquired at considerably higher spatial resolution (0.11 cc) than in the previous series of experiments and clearly delineated the ventricles as shown in FIGS. 6d-f. The SNR of NAA in cortical gray matter was 3-4, which is consistent with previous studies using conventional PEPSI. The subsequent implementation of EVI into the first WS module and integration of GRAPPA acceleration strongly improved signal intensity and image quality (image uniformity, image distortion and ghosting), which were comparable to the multi-slab EVI method of the present embodiment. Activation in the visual cortex was detected after the first task block and the resulting map shows an average correlation coefficient of 0.63 with spatial extent of 71.1 cc and a peak correlation of 0.8 as shown in FIG. 6g. A 4% signal change with contrast-to-noise ratio >10 was measured in a visual cortex as shown in FIG. 6h.

Figure 10K:
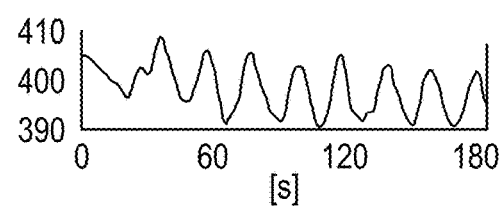
Figure 10G:
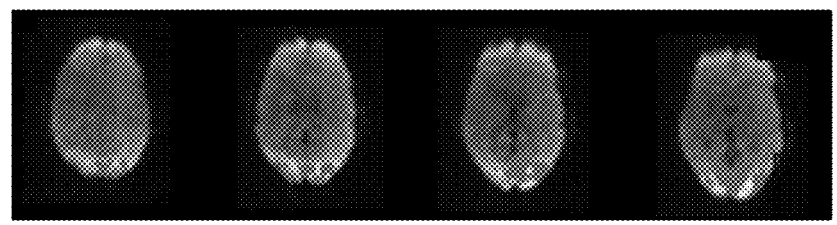
Figure 10I:
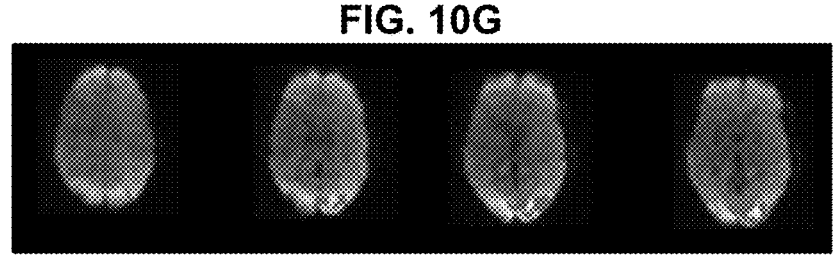
Figure 10J:
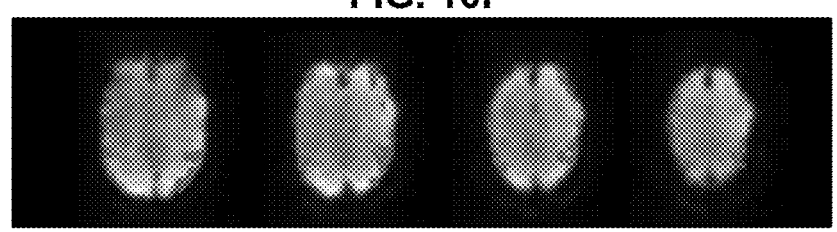
Figure 10L:
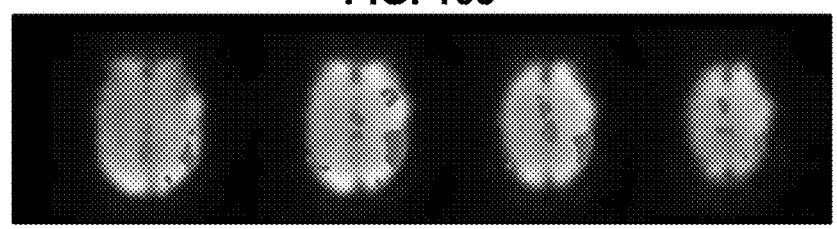

Resting-state connectivity in the visual network was detected in the final 4 minutes of the scan as shown in FIG. 10i. Similar results were obtained in motor cortex as shown in FIGS. 10j-l. Motor activation (FIG. 10j) with signal changes on the order of 5% and high contrast-to-noise (FIG. 10k) were measured in the initial 3 minutes of the scan. Motor resting-state connectivity was detected in the final 4 minutes of the scan (FIG. 10l).

In a preferred embodiment, the present invention concerns a method for acquiring a WR scan concurrently during MRSI acquisition, which provides maximum sensitivity for measuring both metabolites and tissue water in a single acquisition. The embodiment is efficient and minimizes the impact of prolonging TR that is encountered with traditional approaches of interleaving multiple scan acquisitions into an MRSI sequence. When using OVS, which itself increases time delays between the individual WS modules, the integration of the WR acquisition into the first WS module does not significantly increase these WS time delays. This approach requires shortening the readout of the WR signal to a duration on the order of water $T_2$ in gray matter. Although it may impact the precision of water referencing, any change in spectral quantification is expected to be minor given the high SNR of the water signal and the relatively short $T_2^*$ of tissue water. For similar reasons, the effects of the short readout on eddy current correction is expected to be limited.

Nor does interleaving the WR acquisition significantly reduce the performance of water suppression in PEPSI, which employs OVS, since the additional increase in WS delay times is minor. The spectral bandwidth of the WS-RF pulse needs to be large enough to encompass all water frequency offsets in the imaging slab, at the expense of attenuating metabolite signals close to water. Given the known excitation profile of the binomial RF pulse, an intensity correction for off-resonance water signals and metabolite signals within the passband of the binomial RF pulse (e.g. Inositol) could be applied to improve metabolite quantification.

Metabolite concentrations of major singlets and Glutamate/Glutamine that were measured with the embodiments of the present invention were in the range of results published in previous studies both at short and long TE, for spin-echo slice selection and for PRESS prelocalization. Differences in slice profiles and chemical shift displacements between 90 degree and 180 degree RF pulses resulted in chemical shift dependent attenuation of metabolites in 2D data and at the edges of the imaging slab in 3D data, which may have contributed to the differences in NAA concentration between 2D and 3D acquisitions. Differences in slice profiles and chemical shift displacement artifacts between binomial and since RF pulses also may have affected the amplitudes of the WR signals relative to the metabolite signals and thus biased spectral quantification.

Static magnetic field inhomogeneity across large volume requires increased WS bandwidth that can lead to local frequency-shift dependent decreases in water amplitude and suppression of metabolite resonances in the vicinity of the water peak. Mapping of $B_0$ inhomogeneity will assist in predicting these signal changes to correct metabolite concentration values during postprocessing. Alternatively, when segmenting multi-slice/slab MRSI data, it is possible to mitigate the effects of $B_0$ inhomogeneity by modulating the frequency offsets and water-excitation profiles of the binomial RF pulses on a slab/slice-by-slab/slice basis and by using slice/slab-specific shimming. This will also provide more consistent water suppression across larger volumes.

The unusual Cho/Cr contrast in the patient with WHO grade III anaplastic astrocytoma with reduced Cho peak amplitude, and elevated Inositol with possible contributions of Glycine, was not an artifact of the data acquisition. Visual inspection of single-voxel spectra confirmed this metabolite contrast and showed acceptable data quality over the entire sensitive volume. A published case report has similarly described such a finding in a tumor with oligodendroglial neoplastic components, hypothesized to reflect a lesion with low growth fraction.

In other aspects, the present invention concerns a novel hybrid fMRI/MRSI sequence that integrates echo-volumar-imaging and a WR acquisition into the water suppression module of PEPSI to simultaneously acquire fMRI, WS and WR data in a single acquisition. The sensitivity of metabolite mapping was comparable to conventional PEPSI. While this approach slightly reduces the SNR of fMRI and limits the minimum TR compared with conventional fMRI, task-based activation and resting-state connectivity maps were similar to results obtained with conventional fMRI. An approach similar to integrated simultaneous multi-slab encoding into multi-slab EVI may be used to increase the limited volume coverage of the various embodiments. This would also allow implementation of slab-specific shimming to mitigate the $B_0$ offset sensitivity of water-excitation based fMRI. The higher spatial resolution of the PEPSI acquisition in these fMRI/MRSI scans requires considerably longer scan times to achieve acceptable SNR. Task-based fMRI typically requires multiple scans to map different brain functions, which may take 15-30 minutes. Resting-state fMRI in single subjects also requires long scan times, and multiple acquisitions, in excess of 15 minutes. Effective scan times of 15-20 minutes for PEPSI could thus easily be achieved by averaging across fMRI scans, which would support the high spatial resolution of the PEPSI sequence. While the bipolar first WR acquisition in the first WS module is adequate for spectral quantification, frequency-shift and eddy current correction require the second longer WR acquisition embedded in the second WS module. Correction of the k-space signal amplitude and phase of the second longer WR acquisition in reference to the first WR acquisition is currently under investigation. Future work is aimed at further improving quantification by integrating chemical shift displacement correction and real-time navigator-based correction of movement, frequency instability, and phase drifts.

The fPEPSI approach of the present invention to concurrently acquire fMRI and MRSI is generalizable to other MRS acquisition methods including spectral editing. It is therefore applicable to characterizing neurotransmitter and Lactate concentration changes in relation to BOLD signal changes, which has recently attracted considerable interest in neuroscience research. Of particular interest are region-specific measurements of GABA concentrations and concurrent fMRI experiments that map the amplitude of BOLD signal changes during cognitive tasks, which in the past have been acquired separately. The fPEPSI approach further opens up the potential integration of other imaging modalities, such as diffusion tensor imaging or perfusion imaging.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above described embodiments, methods, and examples, but by all embodiments and methods within the scope and spirit of the disclosure.

What is claimed is:

1. A method of concurrently providing Magnetic Resonance Spectroscopic Imaging (MRSI) of water and metabolite signals and functional Magnetic Resonance Imaging (fMRI) of a brain, the method comprising:
    performing, using a Magnetic Resonance Imaging (MRI) scanner, an MRSI data acquisition with a water suppression module, wherein a water readout module is inserted into the water suppression module, whereby MRSI data and fMRI data are acquired concurrently in a single scan;
    reconstructing a water MRSI image of the brain based on the water readout module;
    reconstructing an fMRI image of the brain based on the water readout module;
    outputting the water MRSI image; and
    outputting the fMRI image.

2. A system for concurrently providing Magnetic Resonance Spectroscopic Imaging (MRSI) of water and metabolite signals and functional Magnetic Resonance Imaging (fMRI) of a brain, the system comprising an MRI scanner and an electronic processor communicatively coupled to the Magnetic Resonance Imaging (MRI) scanner and configured to perform operations comprising:
    performing, using the MRI scanner, an MRSI data acquisition with a water suppression module, wherein a water readout module is inserted into the water suppression module, whereby MRSI data and fMRI data are acquired concurrently in a single scan;
    reconstructing a water MRSI image of the brain based on the water readout module;
    reconstructing an fMRI image of the brain based on the water readout module;
    outputting the water MRSI image; and
    outputting the fMRI image.

3. The method of claim 1, wherein the water readout module comprises multiple repetitions of the water suppression module.

4. The method of claim 1, further comprising quantifying metabolite concentrations based on the metabolite signals and the water MRSI image.

5. The method of claim 1, further comprising using the fMRI image to measure at least one of: task-based activation or resting-state connectivity.

6. The method of claim 1, wherein the water suppression module uses a spectral-spatial RF pulse for water excitation to excite a slab.

7. The method of claim 6, wherein the fMRI image comprises data encoded in a single shot within the slab.

8. The method of claim 1, further comprising acquiring navigators during the water suppression module to perform at least one of: correction of movement related phase errors in MRSI and fMRI data, or correction of frequency drifts in MRSI and fMRI data.

9. The method of claim 1, further comprising performing image registration to perform image motion correction across multiple repetitions of the water readout module.

10. The method of claim 1, further comprising using the water readout to perform eddy current correction.

11. The method of claim 1, further comprising using diffusion gradients as part of the water readout module.

12. The system of claim 2, wherein the water readout module comprises multiple repetitions of the water suppression module.

13. The system of claim 2, wherein the operations further comprise quantifying metabolite concentrations based on the metabolite signals and the water MRSI image.

14. The system of claim 2, wherein the operations further comprise using the fMRI image to measure at least one of: task-based activation or resting-state connectivity.

15. The system of claim 2, wherein the water suppression module uses a spectral-spatial RF pulse for water excitation to excite a slab.

16. The system of claim 15, wherein the fMRI image comprises data encoded in a single shot within the slab.

17. The system of claim 2, wherein the operations further comprise acquiring navigators during the water suppression module to perform at least one of: correction of movement related phase errors in MRSI and fMRI data, or perform correction of frequency drifts in MRSI and fMRI data.

18. The system of claim 2, wherein the operations further comprise performing image registration to perform image motion correction across multiple repetitions of the water readout module.

19. The system of claim 2, wherein the operations further comprise using the water readout to perform eddy current correction.

20. The system of claim 2, wherein the operations further comprise using diffusion gradients as part of the water readout module.

* * * * *